(12) United States Patent
Ohtsuka

(10) Patent No.: US 7,648,008 B2
(45) Date of Patent: Jan. 19, 2010

(54) FIXING STRUCTURE FOR IMAGE FORMING APPARATUS

(75) Inventor: Yuzuru Ohtsuka, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 948 days.

(21) Appl. No.: 11/055,120

(22) Filed: Feb. 11, 2005

(65) Prior Publication Data

US 2005/0179878 A1 Aug. 18, 2005

(30) Foreign Application Priority Data

Feb. 16, 2004 (JP) .............................. 2004-038832

(51) Int. Cl.
*F16F 7/10* (2006.01)
*H05G 1/02* (2006.01)

(52) U.S. Cl. ....................... 188/378; 378/197; 378/198; 250/370.09; 296/24.38; 292/40

(58) Field of Classification Search ................. 188/378, 188/380; 378/102, 167, 195, 196, 197, 208, 378/198; 250/582, 370.09; 296/24.38; 292/32, 292/40, 137, 143, 146, 150; 248/638
See application file for complete search history.

(56) References Cited

U.S. PATENT DOCUMENTS

| | | | | |
|---|---|---|---|---|
| 3,845,313 | A | * | 10/1974 | Nosol ........................ 378/208 |
| 3,968,374 | A | * | 7/1976 | Schroeder ................... 378/181 |
| 4,875,228 | A | * | 10/1989 | Archer ....................... 378/197 |
| 5,029,909 | A | * | 7/1991 | Bunger ........................ 292/40 |
| 5,097,497 | A | * | 3/1992 | Deucher et al. ............. 378/204 |
| 5,418,609 | A | | 5/1995 | Dunne |
| 5,509,700 | A | * | 4/1996 | Kennedy, Jr. .................. 292/3 |
| 5,601,274 | A | | 2/1997 | Minor et al. |
| 5,997,176 | A | * | 12/1999 | Fairleigh ..................... 378/196 |
| 6,025,598 | A | | 2/2000 | Tago |
| 6,226,075 | B1 | | 5/2001 | Loopstra et al. |
| 6,481,887 | B1 | | 11/2002 | Mirabella |
| 6,493,062 | B2 | | 12/2002 | Tokuda et al. |

(Continued)

FOREIGN PATENT DOCUMENTS

JP 04-069430 3/1992

(Continued)

OTHER PUBLICATIONS

Chinese Office Action dated Jun. 5, 2009.

(Continued)

*Primary Examiner*—Robert A Siconolfi
*Assistant Examiner*—Thomas W Irvin
(74) *Attorney, Agent, or Firm*—Sughrue Mion, PLLC

(57) ABSTRACT

A second support post supporting a main unit is swingably held by a vibration isolation mechanism on a first support post which is fixedly mounted in a compartment of a vehicle. The second support post supports thereon a first lock for engaging a bracket mounted on a wall of the vehicle to prevent the second support post and the main unit from being swingably displaced. A joint casing on the first support post houses therein a second lock for fixing the second support post to the first support post. When the vehicle is stopped for the main unit to capture an image of a subject, the first and second locks fix the main unit to the vehicle.

14 Claims, 12 Drawing Sheets

U.S. PATENT DOCUMENTS

| | | | |
|---|---|---|---|
| 6,508,087 B2 * | 1/2003 | Lemley et al. | 70/56 |
| 6,512,571 B2 | 1/2003 | Hara | |
| 6,625,252 B2 * | 9/2003 | Mirabella | 378/102 |
| 6,626,412 B1 | 9/2003 | Lindsay | |
| 7,252,182 B2 * | 8/2007 | Ohtsuka | 188/378 |
| 2002/0014594 A1 | 2/2002 | Endo | |
| 2004/0000794 A1 * | 1/2004 | Wang | 292/143 |

FOREIGN PATENT DOCUMENTS

| | | |
|---|---|---|
| JP | 6-68728 U | 9/1994 |
| JP | 10-171047 | 6/1998 |
| JP | 10-246999 A | 9/1998 |
| JP | 2001-128962 A | 5/2001 |
| JP | 2001-299743 A | 10/2001 |
| JP | 2002-278003 A | 9/2002 |
| JP | 2005-087536 | 4/2005 |

OTHER PUBLICATIONS

Japanese Office Action dated Jul. 14, 2009.
Japanese Office Action date Sep. 9, 2008, with partial translation (3 pages).

* cited by examiner

FIXING STRUCTURE FOR IMAGE FORMING APPARATUS

BACKGROUND OF THE INVENTION

1. Field of the Invention

The present invention relates to an image forming apparatus for being mounted on a vehicle, and more particularly to a fixing structure for fixing an exposure unit of an image forming apparatus to and releasing the exposure unit from a vehicle, the image forming apparatus having a vibration isolation structure for suppressing vibration transmitted from the vehicle.

2. Description of the Related Art

There have heretofore been known image forming apparatus for recording radiation image information of a subject such as a human body on a stimulable phosphor sheet having a stimulable phosphor layer. A stimulable phosphor is a phosphor which, when exposed to an applied radiation (X-rays, α-rays, β-rays, γ-rays, electron beams, ultraviolet radiation, or the like), stores part of the energy of the radiation, and, when subsequently exposed to applied stimulating rays such as visible light, emits photostimulated luminescence in proportion to the stored energy of the radiation.

An image forming apparatus disclosed in Japanese Laid-Open Patent Publication No. 2001-299743 is installed on a vehicle such as a mobile medical examination car and mounted on the chassis of the mobile medical examination car. The disclosed image forming apparatus can take pictures of subjects for medical examination within the vehicle and at remote sites.

Generally, image forming apparatus for use on vehicles have optical systems that are subject to vibrations. For example, Japanese Laid-Open Patent Publication No. 2001-299743 discloses an image forming apparatus comprising a medical image scanner for scanning patient's bodies. When the image forming apparatus is installed on a vehicle, the optical system thereof is subject to vibrations from the wheels of the vehicle while the vehicle is being driven or vibrations from the engine or electric generator on the vehicle, and may tend to decrease in function.

Heretofore, the image forming apparatus for use on vehicles have not been equipped with a vibration suppressing mechanism for blocking vibrations from being applied from the vehicle to the optical system. Consequently, since the optical system decreases more in function as the resolution of the image forming unit of the image forming apparatus for reading images is higher, it has been difficult to install highly accurate image forming apparatus on vehicles.

Japanese Laid-Open Patent Publication No. 10-246999 discloses a structure for fixing an image forming apparatus to a floor to prevent it from falling by an engaging member mounted on a plate disposed on the floor and held in engagement with a plurality of engaged members on a lower portion of the image forming apparatus.

However, Japanese Laid-Open Patent Publication No. 10-246999 discloses or suggests nothing about a vibration suppressing mechanism for blocking vibrations from being applied from the vehicle to the optical system mounted on the vehicle.

The applicant of the present application has proposed a vibration isolation mechanism mounted on a support post fixed to a vehicle and a holder holding an exposure unit having an optical system through the vibration isolation mechanism. The vibration isolation mechanism holds the holder to prevent vibrations from being transmitted from the vehicle to the exposure unit.

SUMMARY OF THE INVENTION

It is a general object of the present invention to provide a fixing structure for an image forming apparatus mounted on a vehicle, the fixing structure being capable of easily fixing an exposure unit of the image forming apparatus to the vehicle and releasing the exposure unit from the vehicle.

According to the present invention, when a vehicle is stopped for an exposure unit to capture a radiation image of a subject, a holder which holds the exposure unit is fixed to the vehicle and a support post by a fixing mechanism. When the vehicle is to be driven, the fixing mechanism releases the holder from the vehicle and the support post. Therefore, the holder holding the exposure unit can selectively be fixed to and released from the vehicle by the fixing mechanism.

While the vehicle is being driven, since the holder is released from the vehicle, vibrations are prevented from being transmitted from the vehicle to the exposure unit held by the holder. When the vehicle is stopped for the exposure unit to capture a radiation image of the subject, the fixing mechanism fixes the holder to the vehicle. The exposure unit which is now prevented from being displaced with respect to the vehicle can stably capture a radiation image of the subject.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
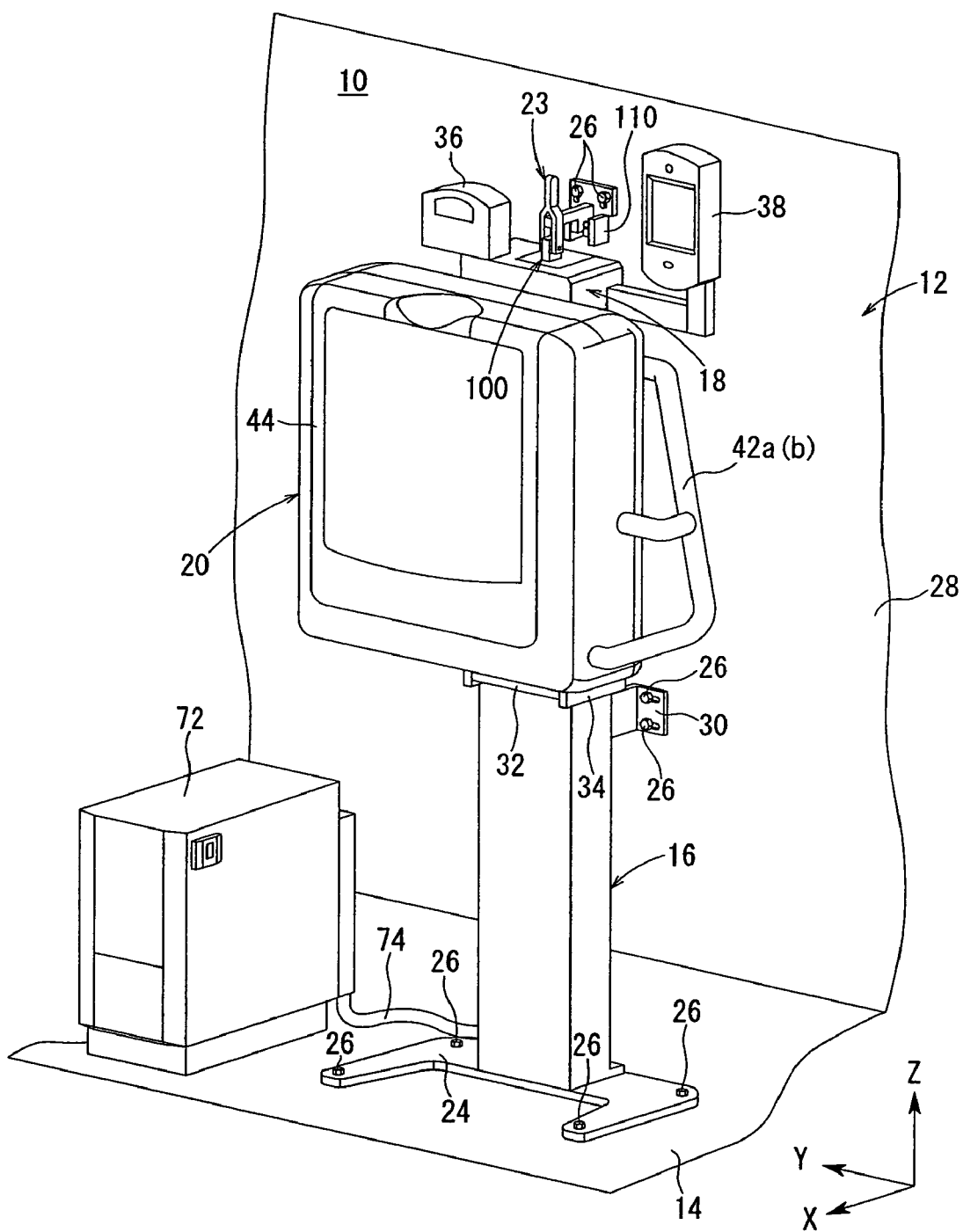
FIG. 1 is a front perspective view showing an image forming apparatus incorporating a vibration isolation mechanism according to an embodiment of the present invention, which is installed in a compartment of a vehicle.

FIG. 1 shows in fragmentary perspective an image forming apparatus 10 incorporating a fixing structure according to an embodiment of the present invention, which is installed in a compartment of a vehicle.

Figure 2:
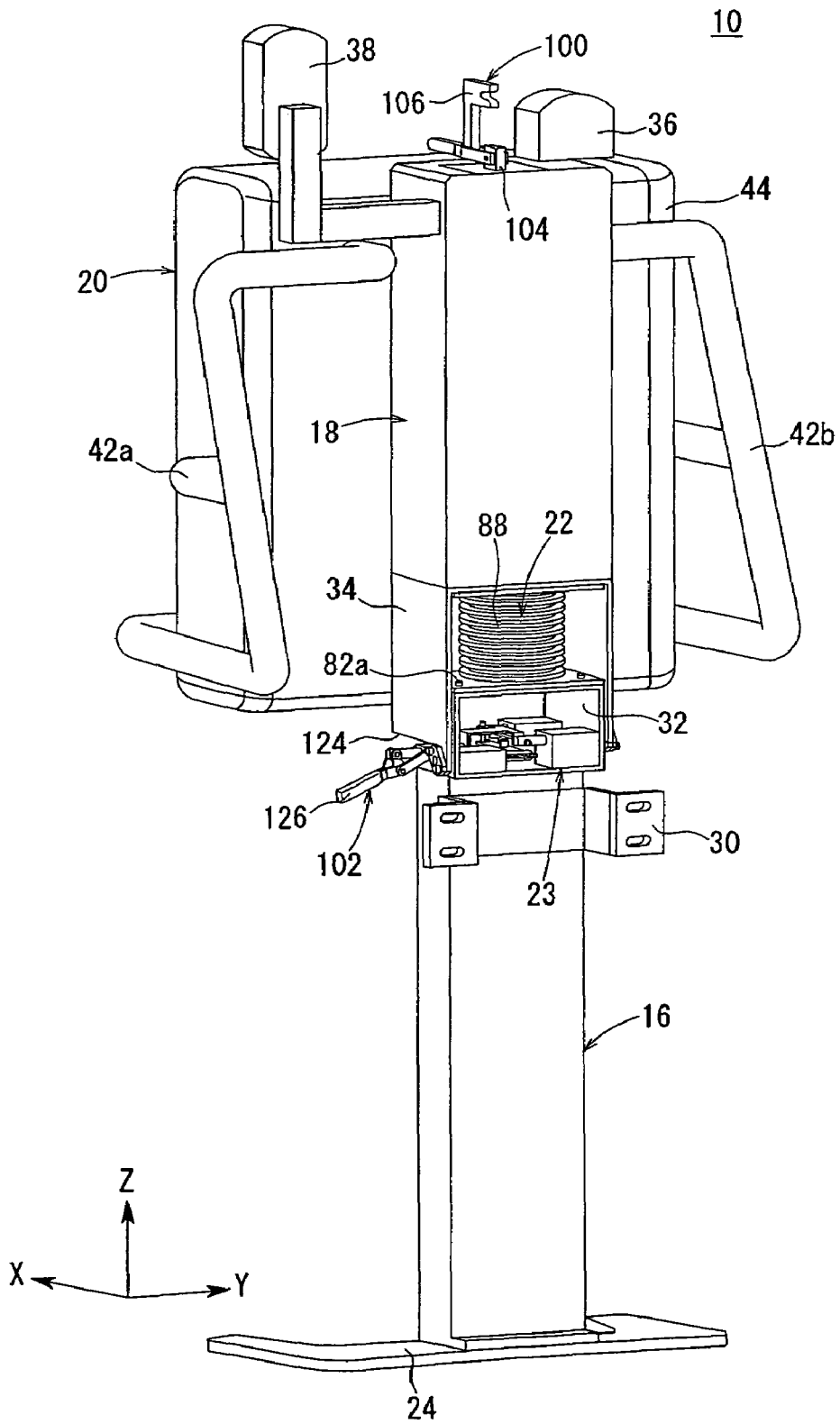
FIG. 2 is a rear perspective view of the image forming apparatus shown in FIG. 1, as viewed from a wall surface of the vehicle.

As shown in FIGS. 1 and 2, the image forming apparatus 10 has a first support post (support post) 16 erected on a floor 14 of a vehicle 12 (see FIG. 12), a second support post (holder) 18 (see FIG. 2) formed separately from and mounted on an upper end of the first support post 16, a main unit (exposure unit) 20 supported on the second support post 18 for vertical movement along its vertical axis, a vibration isolation mechanism (vibration suppressing mechanism) 22 (see FIG. 2) for suppressing vibration transmitted from the vehicle 12 to the main unit 20 and for connecting the first support post 16 to the second support post 18, and a fixing mechanism 23 for fixing the main unit 20 to the vehicle 12 when an image of a subject 40 (see FIG. 3) is captured by the main unit 20.

The first support post 16 has a substantially rectangular horizontal cross section and includes a plate-like support base 24 disposed on the lower end thereof and lying substantially perpendicularly to the axis of the first support post 16. The support base 24 is fastened to the floor 14 in the compartment of the vehicle 12 by mounting bolts 26 (see FIG. 1).

A fixing bracket 30 is mounted on the upper end of the first support post 16 in facing relation to a wall 28 of the vehicle 12 which extends substantially perpendicularly to the floor 14. The first support post 16 is secured to the wall 28 by the fixing bracket 30 which is fastened to the wall 28 by mounting bolts 26. Therefore, the first support post 16 is firmly mounted in the compartment of the vehicle 12 by two members, i.e., the support base 24 and the fixing bracket 30.

As shown in FIG. 2, a box-shaped joint casing 32 is mounted on the upper end of the first support post 16. The fixing mechanism 23 includes a second lock (second fixture) 102 (described later on) mounted on a side wall of the joint casing 32, and the vibration isolation mechanism 22 is mounted on an upper wall of the joint casing 32.

The second support post 18 also has a substantially rectangular horizontal cross section. A storage casing 34 having a substantially channel-shaped cross section which is open toward the first support post 16 is provided on the lower end of the second support post 18. The storage casing 34 stores therein the joint casing 32 mounted on the upper end of the first support post 16 and the vibration isolation mechanism 22. As shown in FIG. 2, the joint casing 32 has opposite side walls covered with respective side walls of the storage casing 34 which extend downwardly over the joint casing 32.

As shown in FIG. 1, a display unit 36 and a console panel 38 are mounted on the upper end of the second support post 18. The display unit 36 has a function to display instructions to be read by a patient as a subject 40 (see FIG. 3) for capturing an image of the subject 40. The console panel 38 is operated by the operator to activate the image forming apparatus 10, and has a function to display patient information, an exposure size, selectable items, and utility control information.

Figure 3:
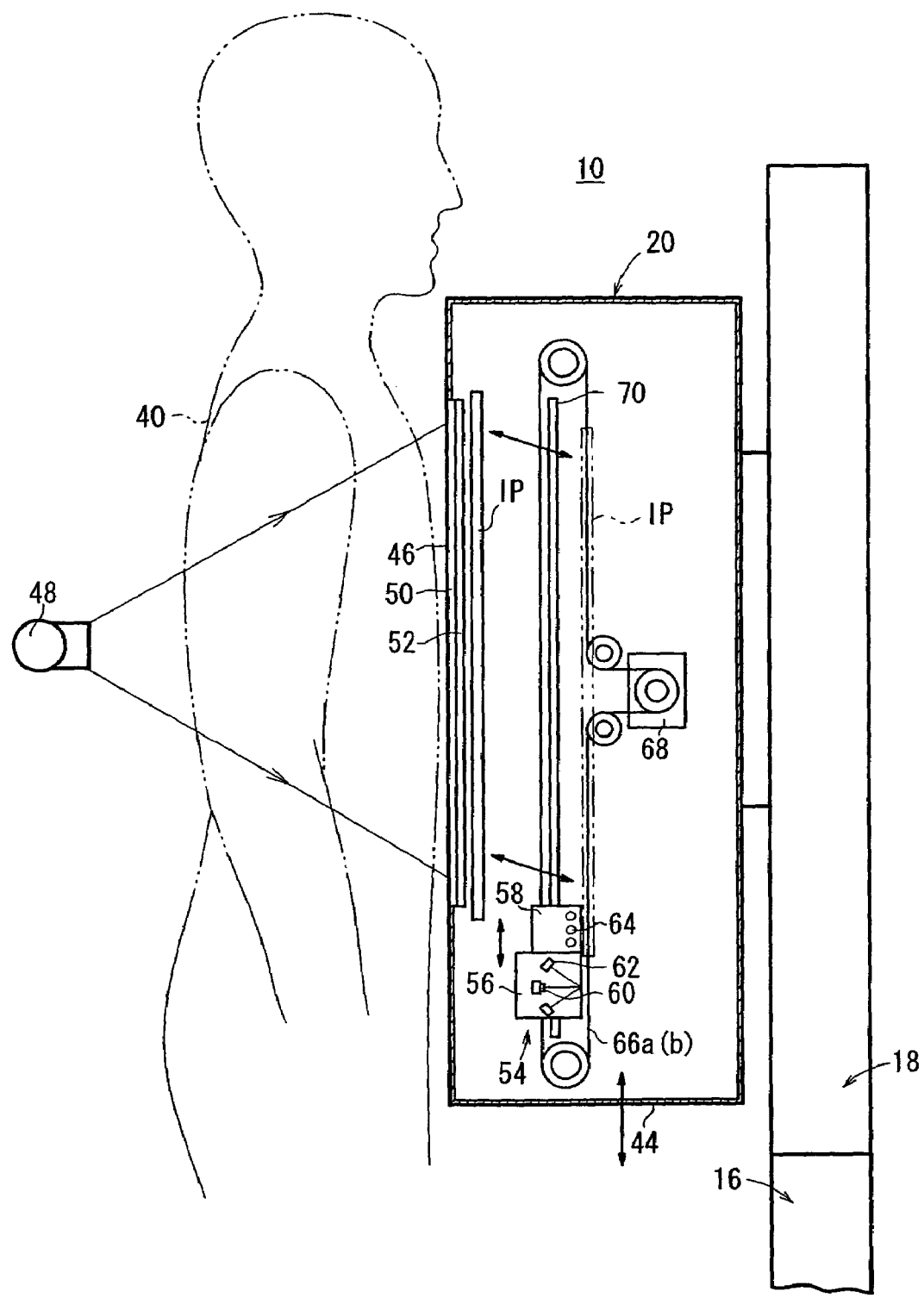
FIG. 3 is a fragmentary vertical cross-sectional view of a main unit and other components of the image forming apparatus shown in FIG. 1.

The main unit 20 has a pair of grip bars 42a, 42b (see FIG. 2) mounted on its opposite sides for the subject 40 (see FIG. 3) to grip to keep its posture for capturing its image. As shown in FIG. 3, the main unit 20 has a box-shaped housing 44 including a front panel serving as an exposure base 46 for positioning the subject 40 thereon. The exposure base 46 is combined with a phototimer 50 for measuring a dose of X-rays applied from a radiation source 48 through the subject 40 to control the amount of radiation to be applied, and a grid 52 for removing scattered rays.

The main unit 20 accommodates therein a stimulable phosphor sheet IP that is movable between a position (indicated by the solid lines) close to the grid 52 and a position (indicated by the two-dot-and-dash lines) remote from the grid 52.

The main unit 20 also houses therein a reading/erasing unit 54 that is vertically movable along the front surface of the stimulable phosphor sheet IP which is in the position indicated by the two-dot-and-dash lines. The reading/erasing unit 54 comprises a reader 56 for applying stimulating light to the stimulable phosphor sheet IP and photoelectrically reading photostimulated luminescence emitted from the stimulable phosphor sheet IP depending on the intensity of radiation energy stored in the stimulable phosphor sheet IP as representing radiation image information, and an eraser 58 for applying erasing light to the stimulable phosphor sheet IP from which the radiation image information has been read to remove any remaining radiation energy from the stimulable phosphor sheet IP.

The reader 56 comprises a plurality of light sources 60 each having a laser diode for emitting stimulating light, and a plurality of CCD line sensors 62 for converting the photostimulated luminescence emitted from the stimulable phosphor sheet IP into an electric signal. The eraser 58 comprises a plurality of light sources 64 for emitting erasing light.

The reading/erasing unit 54 is connected to feed belts 66a, 66b which are driven by a reading/erasing unit moving motor 68 to move the reading/erasing unit 54 vertically along guide rails 70 which extend vertically on both sides of the stimulable phosphor sheet IP.

As shown in FIG. 1, a controller 72 for controlling the image forming apparatus 10 is disposed outside of the main unit 20. The controller 72 is connected to the main unit 20 by a cable 74.

Figure 4:
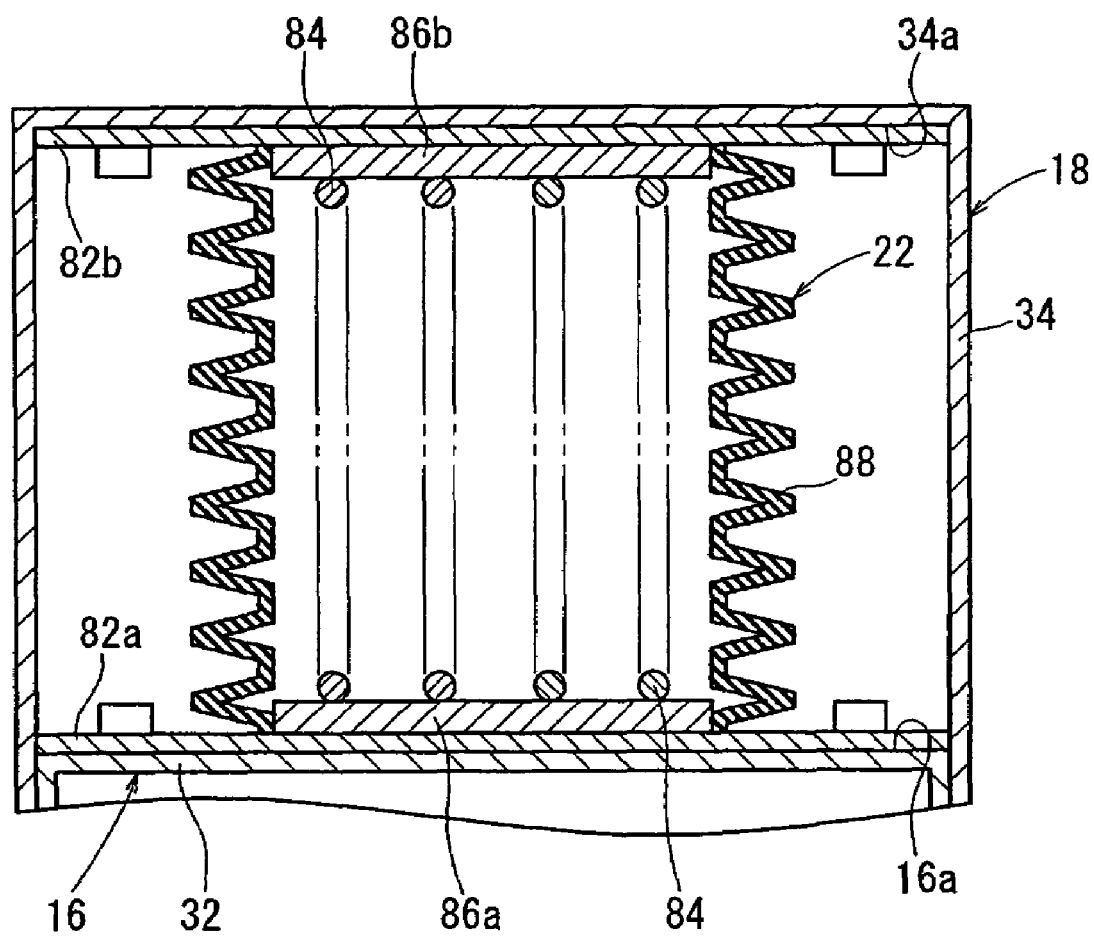
FIG. 4 is an enlarged vertical cross-sectional view of a vibration isolation mechanism shown in FIG. 2.

As shown in FIG. 4, the vibration isolation mechanism 22 comprises a first joint plate 82a fixed to an upper end surface 16a of the joint casing 32 on the first support post 16, a second joint plate 82b fixed to an inner wall surface 34a of the storage casing 34 on the second support post 18 which is spaced upwardly from and faces the upper end surface 16a of the joint casing 32, a spring (resilient member) 84 such as helical springs, for example, interposed between the first and second joint plates 82a, 82b, and a cylindrical cover member 88 interposed between retainers 86a, 86b mounted respectively on the first and second joint plates 82a, 82b in covering relation to the spring 84.

The spring 84 comprises a plurality of equally spaced springs interconnecting the first and second joint plates 82a, 82b. The spring 84 has optimum characteristics, e.g., spring characteristics, material characteristics, etc., depending on the weights and the positions of the center of gravity of the second support post 18 and the main unit 20 which are supported by the vibration isolation mechanism 22, or various conditions such as vibrating conditions of the vehicle 12 while the vehicle 12 is being driven.

The second support post 18 and the main unit 20 which are supported on and above the vibration isolation mechanism 22 are held by the spring 84 of the vibration isolation mechanism 22 for three-dimensional swinging movement by predetermined distances along X-, Y-, and Z-axes with respect to the first support post 16.

Instead of the spring 84, a resilient body such as of rubber or the like, which may comprise a plurality of resilient members, may be interposed between the first and second joint plates 82a, 82b and disposed in the cover member 88. Both such a resilient body and the spring 84 may be interposed between the first and second joint plates 82a, 82b and disposed in the cover member 88. Stated otherwise, the vibration isolation mechanism 22 may have any means for damping vibration transmitted from the vehicle 12 through the first support post 16 to the second support post 18 and hence to the main unit 20.

The number of springs of the spring 84 and/or the number of resilient members of the resilient body is not limited to any particular value. The spring 84 may comprise a single spring or a plurality of springs, and the resilient body may comprise a single resilient member or a plurality of resilient members depending on the weights and the positions of the center of gravity of the second support post 18 and the main unit 20, or various conditions such as vibrating conditions of the vehicle 12 while the vehicle 12 is being driven.

As shown in FIGS. 1 and 2, the fixing mechanism 23 comprises a first lock (first fixture) 100 mounted on the upper end of the second support post 18 for fixing the main unit 20 to the wall 28 of the vehicle 12 through the second support post 18, and a second lock (second fixture) 102 mounted in the joint casing 32 on the first support post 16 for securing the first support post 16 and the second support post 18 integrally to each other.

Figure 5:
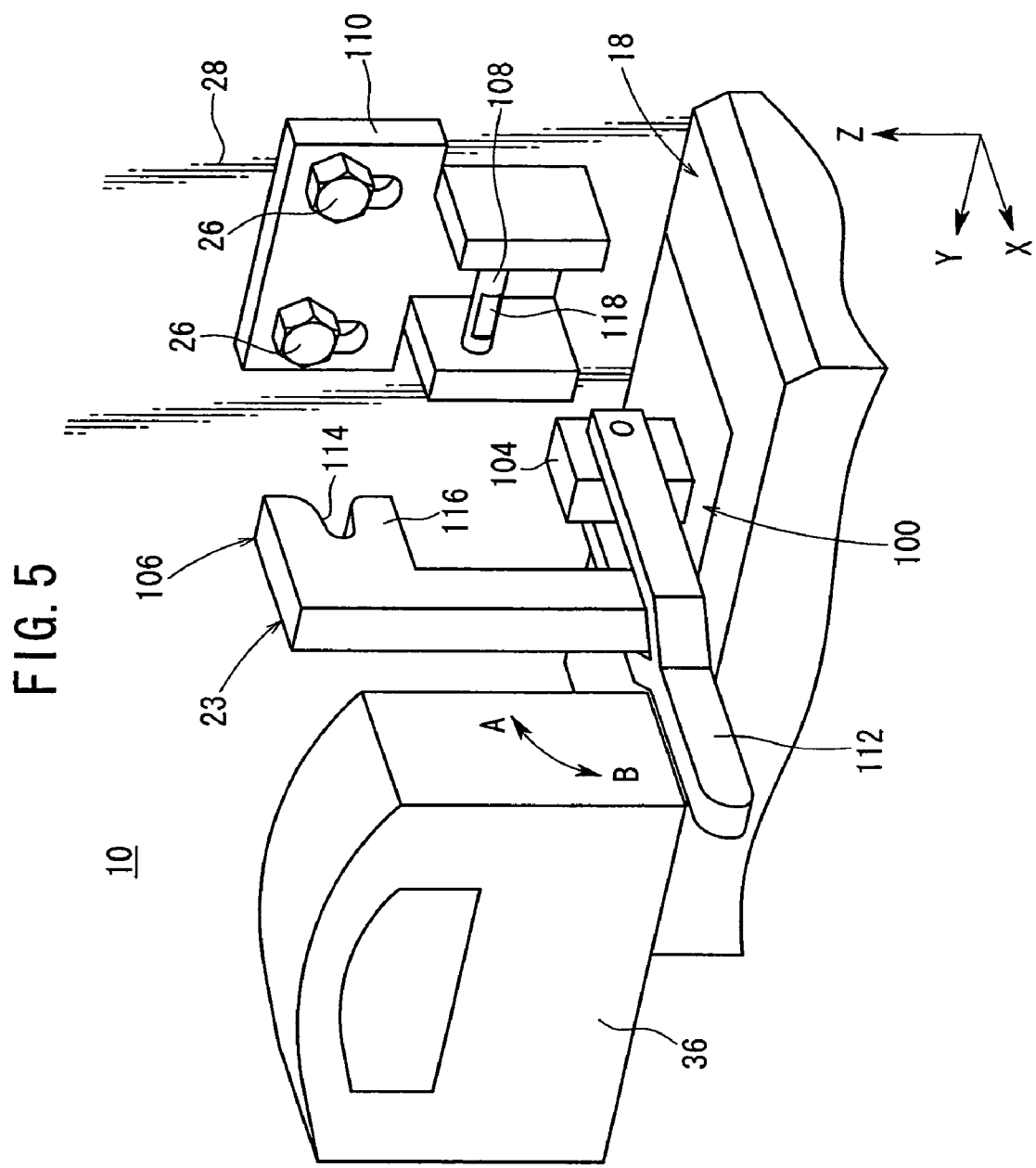
FIG. 5 is an enlarged fragmentary perspective view of a first lock of the fixing mechanism shown in FIG. 1 which is mounted on an upper end of a second support post.
Figure 6:
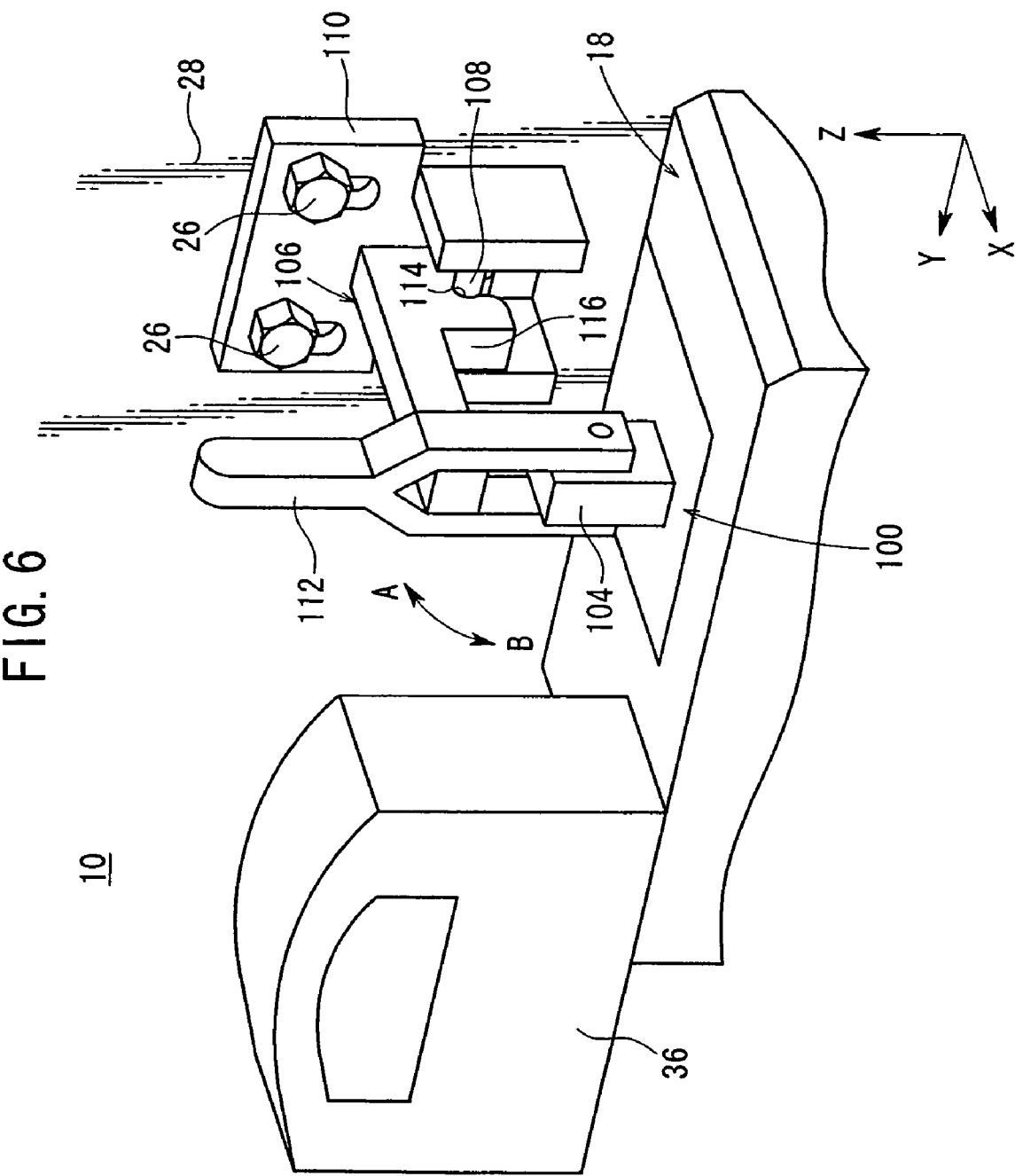
FIG. 6 is an enlarged fragmentary perspective view showing the manner in which the second support post is fixed to the wall surface of the vehicle by the first lock shown in FIG. 5.

As shown in FIGS. 5 and 6, the first lock 100 comprises a support member 104 mounted on the upper end surface of the second support post 18, and a lock arm (clamp arm) 106 angularly movably supported on the support member 104. A bracket (engaging member) 110 having a substantially horizontal pin 108 is mounted by mounting bolts 26 to the wall 28 of the vehicle 12 which faces the first lock 100.

The lock arm 106 comprises a grip lever 112 which can be gripped and turned about the support member 104 by the operator and a clamp 116 extending substantially perpendicularly to the grip lever 112, the clamp 116 having an engaging slot 114 of a substantially U-shaped cross section. The engaging slot 114 is open toward the bracket 110. The clamp 116 is joined to an intermediate portion of the lock arm 106, which has a grip end and an opposite end that is pivotally supported on the support member 104.

The lock arm 106 operates as follows: If the grip lever 112 is turned toward the wall 28 of the vehicle 12 in the direction indicated by the arrow A, then the turning movement of the grip lever 112 is limited when the grip lever 112 extends vertically, i.e., substantially perpendicularly to the upper end surface of the second support post 18 (see FIG. 6). Conversely, if the grip lever 112 is turned away from the wall 28 of the vehicle 12, i.e., toward the display unit 36, in the direction indicated by the arrow B, then the turning movement of the grip lever 112 is limited when the grip lever 112 extends substantially horizontally, i.e., parallel to the upper end surface of the second support post 18 (see FIG. 5). Stated otherwise, the lock arm 106 is angularly movable through 90° with respect to the support member 104.

When the grip lever 112 is turned toward the wall 28 of the vehicle 12 in the direction indicated by the arrow A, the clamp 116 is turned toward the bracket 110 on the wall 28, causing the engaging slot 114 in the clamp 116 to fit over the pin 108 of the bracket 110. The second support post 18 and the main unit 20 are now prevented from being displaced toward and away from the wall 28 in the directions of the X-axis by the lock arm 106 of the first lock 100 (see FIG. 6).

As shown in FIG. 5, the pin 108 has a recess 118 defined centrally therein in its front side and extending in the axial direction of the pin 108 over a predetermined distance substantially equal to the width of the clamp 116. When the engaging slot 114 in the clamp 116 fits over the pin 108, the clamp 116 is engaged by the opposite ends of the recess 118, preventing the second support post 18 and the main unit 20 from being displaced substantially parallel to the wall 28 in the directions of the Y-axis (see FIG. 6).

Accordingly, the second support post 18 and the main unit 20 are firmly secured to the wall 28 by the first lock 100 and the bracket 110.

When the grip lever 112 is turned away from the wall 28 of the vehicle 12 in the direction indicated by the arrow B, the clamp 116 is turned away from the pin 108 in the direction indicated by the arrow B. Since the clamp 116 is released from the first lock 100, the second support post 18 and the main unit 20 are disconnected from the wall 28 (see FIG. 5).

Figure 7:
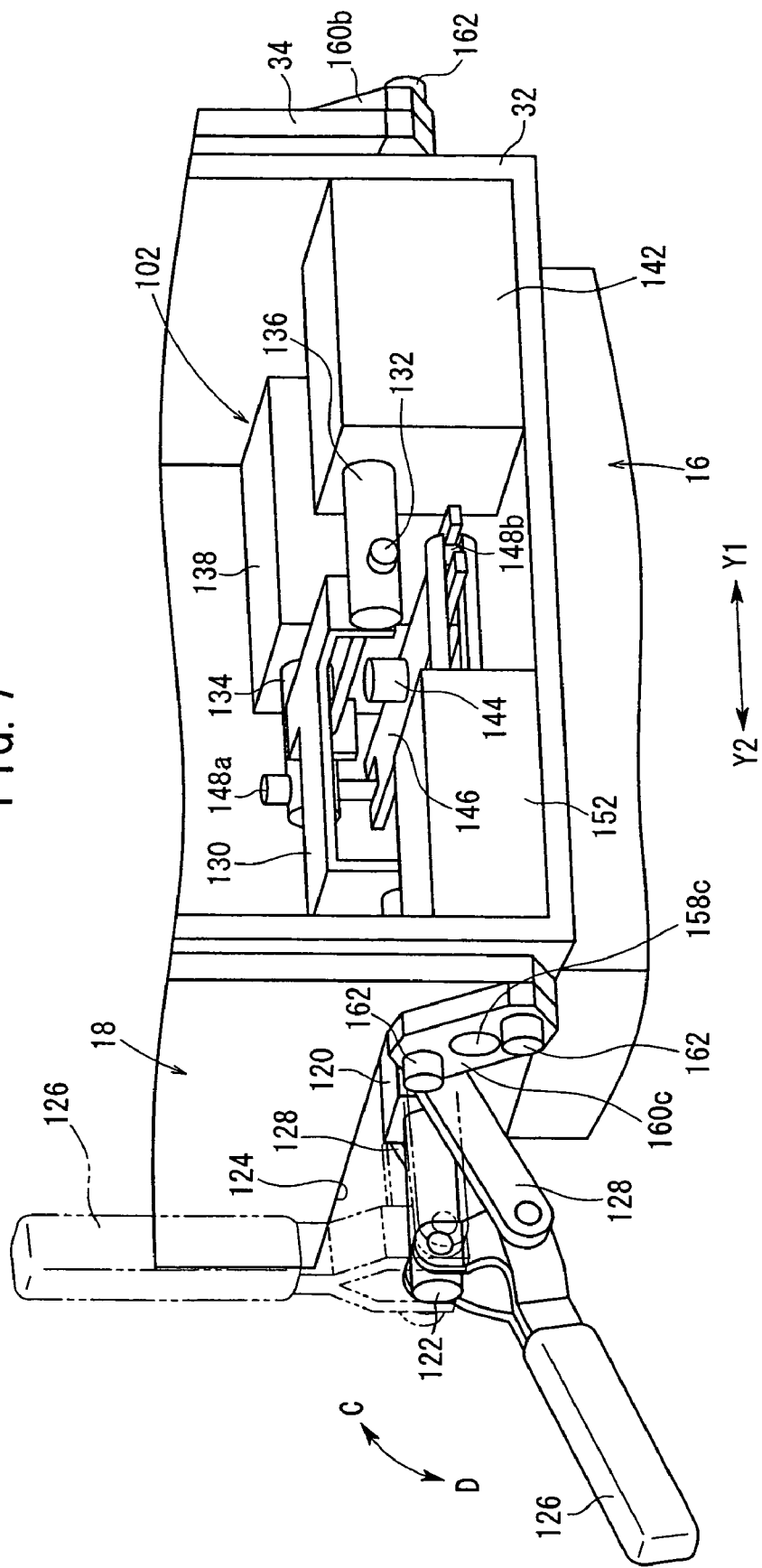
FIG. 7 is an enlarged fragmentary perspective view of a second lock of the fixing mechanism shown in FIG. 2.

As shown in FIG. 7, the second lock 102 has a shaft 122 extending through a guide block 120 fixedly mounted in the joint casing 32 (see also FIGS. 10 and 11) and guided thereby for displacement in its axial directions indicated by the arrows Y1, Y2. The shaft 122 extends substantially parallel to the main unit 20 and has an end projecting out of the joint casing 32 through an opening 124 that is defined in side walls of the joint casing 32 and the storage casing 34.

The second lock 102 also has a grip lever (operating lever) 126 attached to an end of the shaft 122. The grip lever 126 can be gripped by the operator to selectively lock the second support post 18 to the first support post 16 and unlock the second support post 18 from the first support post 16. The grip lever 126 is angularly movable about 90° about the end of the shaft 122 upwardly from a substantially horizontal position.

A pair of holder arms 128 has respective ends pivotally supported on the grip lever 126 at a position that is spaced a predetermined distance from the portion of the grip lever 126 that is pivotally supported on the shaft 122. The holder arms 128 have other ends pivotally supported on respective opposite sides of the guide block 120. When the grip lever 126 is turned upwardly in the direction indicated by the arrow C toward the joint casing 32, the grip lever 126 and the holder arms 128 are turned from the solid-line position to the two-dot-and-dash-line position shown in FIG. 7. The shaft 122 that is pivotally connected to the grip lever 126 is pushed into the joint casing 32, i.e., displaced in the direction indicated by the arrow Y1.

Conversely, when the grip lever 126 is turned in the direction indicated by the arrow D away from the joint casing 32, the grip lever 126 and the holder arms 128 are turned from the two-dot-and-dash-line position to the solid-line position, pulling the shaft 122 out of the joint casing 32, i.e., displacing the shaft 122 in the direction indicated by the arrow Y2.

That is, when the grip lever 126 that is limited against free angular movement by the holder arms 128 is turned in the directions indicated by the arrows C, D, the shaft 122 inserted in the guide block 120 can be displaced axially in the directions indicated by the arrows Y1, Y2.

Figure 10:
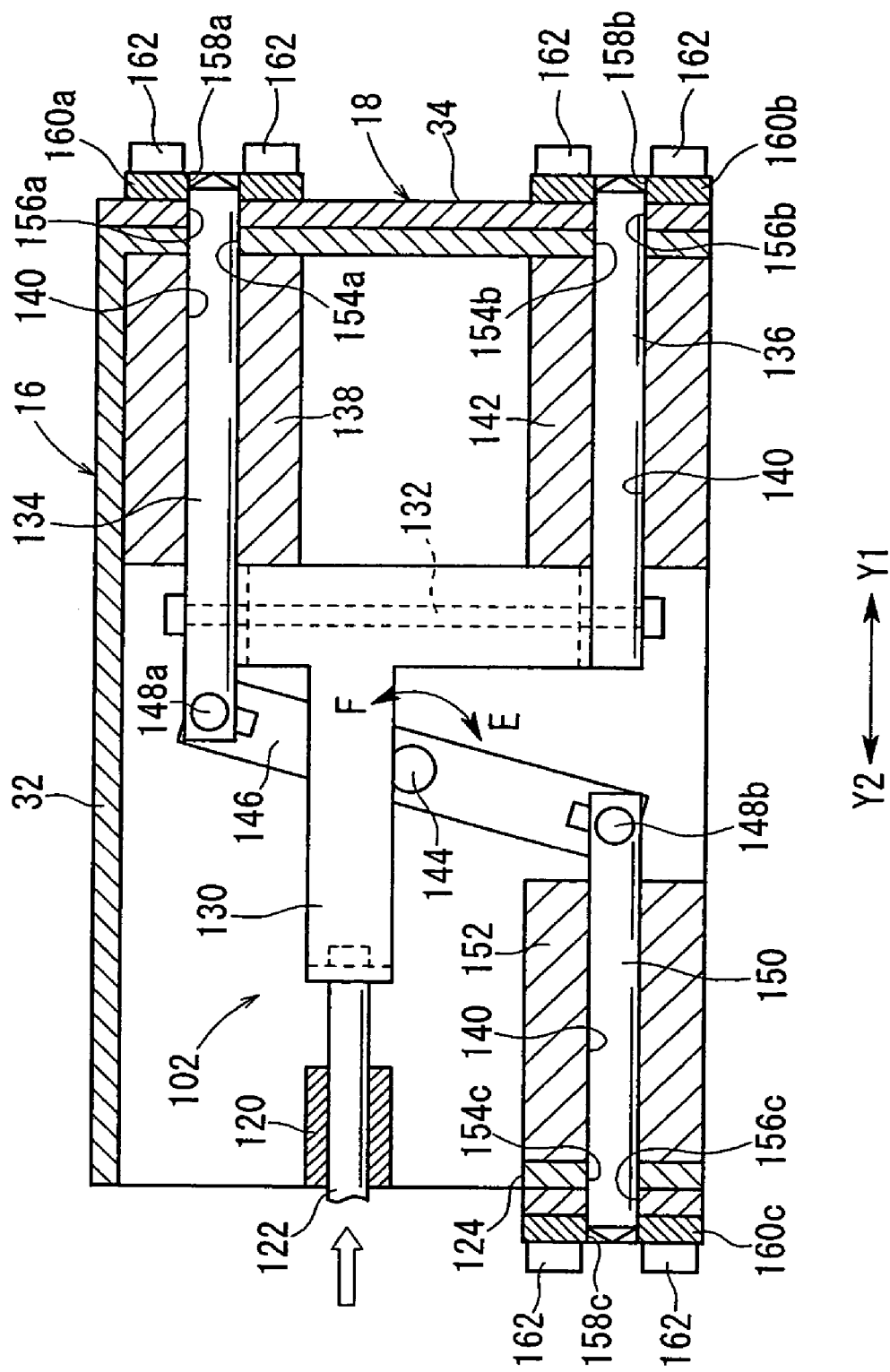
FIG. 10 is a horizontal cross-sectional view showing the manner in which first through third lock pins of the second lock shown in FIG. 7 extend through walls of a joint casing and the storage casing, joining the first support post to a second support post.
Figure 11:
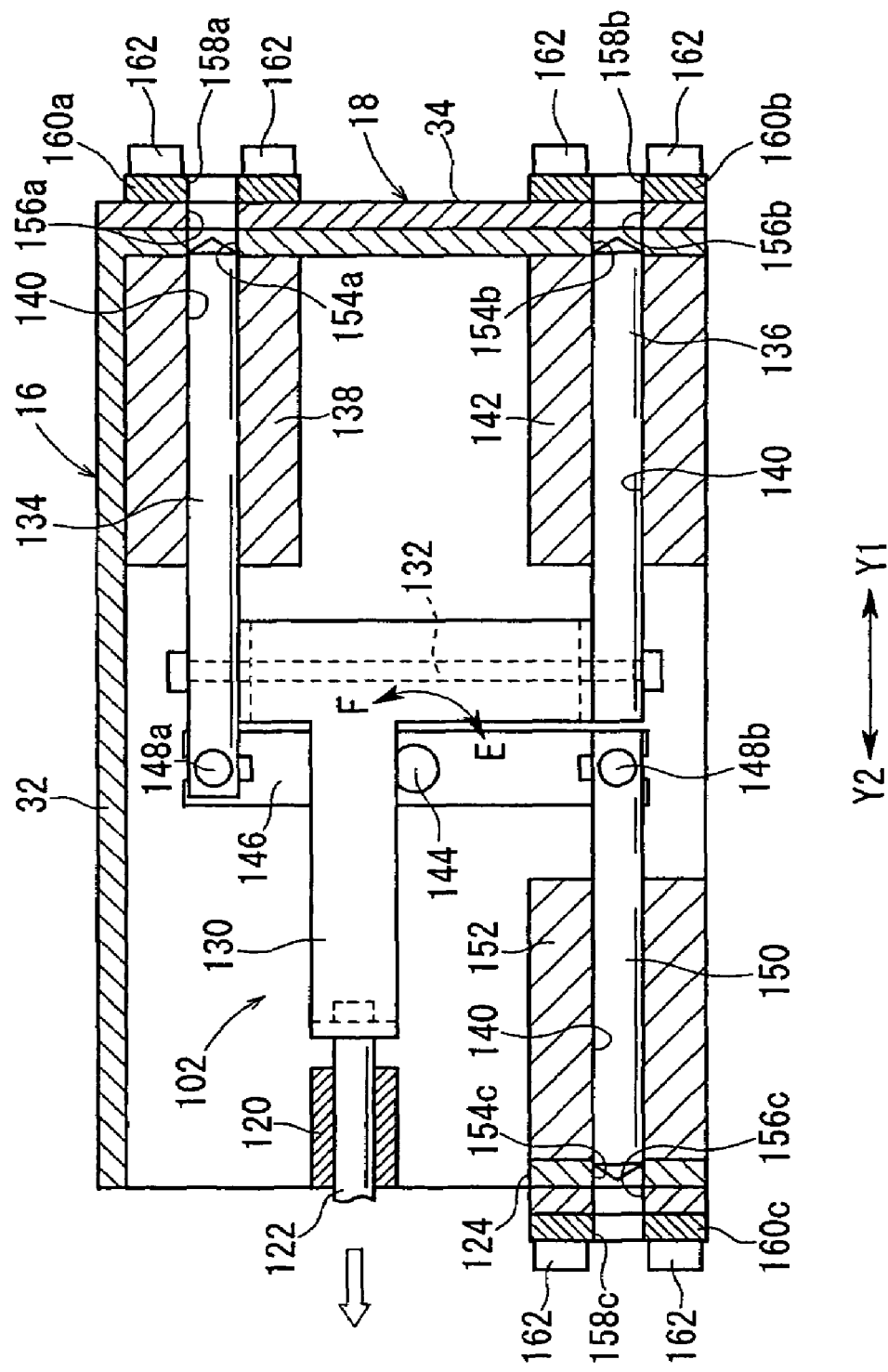
FIG. 11 is a horizontal cross-sectional view showing the manner in which the first through third lock pins of the second lock shown in FIG. 10 are retracted into the joint casing, releasing the first support post from the second support post.

As shown in FIGS. 7, 10, and 11, a substantially T-shaped connector 130 has an end joined to the other end of the shaft 122 which is located in the joint casing 32. The other end of the connector 130 has an arm extending perpendicularly to the axis thereof, and the arm has opposite ends supporting an elongate engaging pin 132 which extends through holes defined respectively in those opposite ends. The engaging pin 132 extends perpendicularly through ends of first and second lock pins 134, 136.

The first and second lock pins 134, 136 are spaced a predetermined distance from each other and extend substantially parallel to each other from the other end of the connector 130 away from the grip lever 126 in the direction indicated by the arrow Y1. The first and second lock pins 134, 136 lie substantially perpendicularly to the other end of the connector 130.

The first and second lock pins 134, 136 are of a cylindrical shape, and have substantially equal lengths along the axial directions thereof which are indicated by the arrows Y1, Y2. The first lock pin 134 extends through a through hole 140 defined in a first holder block 138 which is held against one of the side walls of the joint casing 32 and disposed in the joint casing 32 closely to the main unit 20. The second lock pin 136 extends through a through hole 140 defined in a second holder block 142 which is held against the same side wall of the joint casing 32 substantially parallel to the first holder block 138 and disposed in the joint casing 32 remotely from to the main unit 20.

A support pin 144 is mounted substantially centrally in the joint casing 32 and extends substantially parallel to the axis of the first support post 16. A link arm 146 is angularly movably mounted on the support pin 144 for angular movement about the support pin 144. The link arm 146 has an end engaging a link pin 148a which is mounted on an end of the first lock pin 134 that is positioned out of the first holder block 138. As shown in FIGS. 10 and 11, the link arm 146 is pivotally supported on the first lock pin 134 at a position closer to the grip lever 126 in the direction indicated by the arrow Y2 than the position where the engaging pin 132 extends through the first lock pin 134.

The other end of the link arm 146 engages a link pin 148b mounted on an end of a third lock pin 150.

The link arm 146 is thus angularly movable about the support pin 144 when the first and third lock pins 134, 150 are axially displaced.

The third lock pin 150 is of a cylindrical shape and is disposed alongside of the guide block 120 in substantial alignment with the second lock pin 136. The third lock pin 150 extends through a through hole 140 defined in a third holder block 152 which is held against the other side wall of the joint casing 32 and disposed in the joint casing 32 remotely from the main unit 20.

The side wall of the joint casing 32 which is held against the first and second holder blocks 138, 142 has first holes 154a, 154b defined therein in alignment with the respective through holes 140 in the first and second holder blocks 138, 142.

The side wall of the joint casing 32 which is held against the third holder block 152 also has a first hole 154c defined therein in alignment with the through hole 140 in the third holder block 152.

The side walls of the storage casing 34 which face the respective side walls of the joint casing 32 have second holes 156a, 156b, 156c defined therein and having respective diameters substantially equal to those of the first holes 154a, 154b, 154c, respectively. The through holes 140 in the first, second, and third holder blocks 138, 142, 152 are held in communication with the first holes 154a, 154b, 154c, respectively, in the joint casing 32 and also with the second holes 156a, 156b, 156c, respectively, in the storage casing 34 (see FIGS. 10 and 11).

Figure 8:
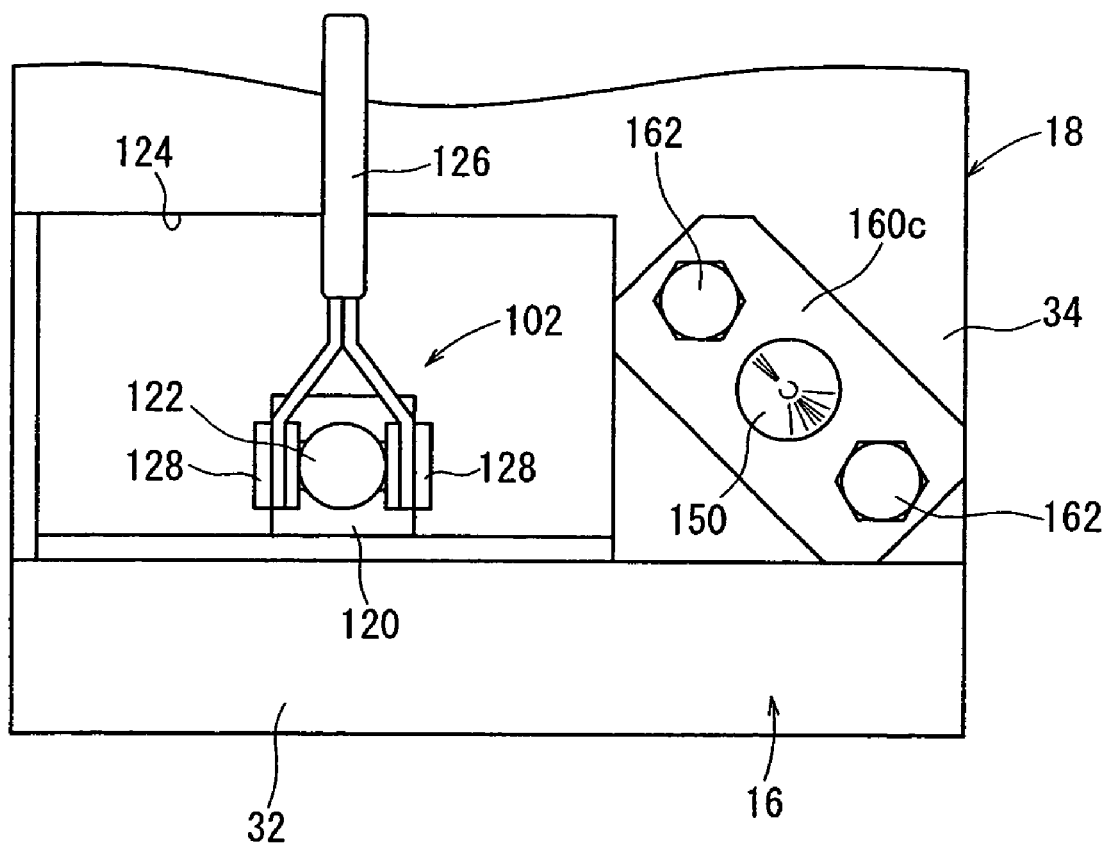
FIG. 8 is an enlarged right side elevational view of a storage casing of the second support post, as viewed from the right side of the image forming apparatus.
Figure 9:
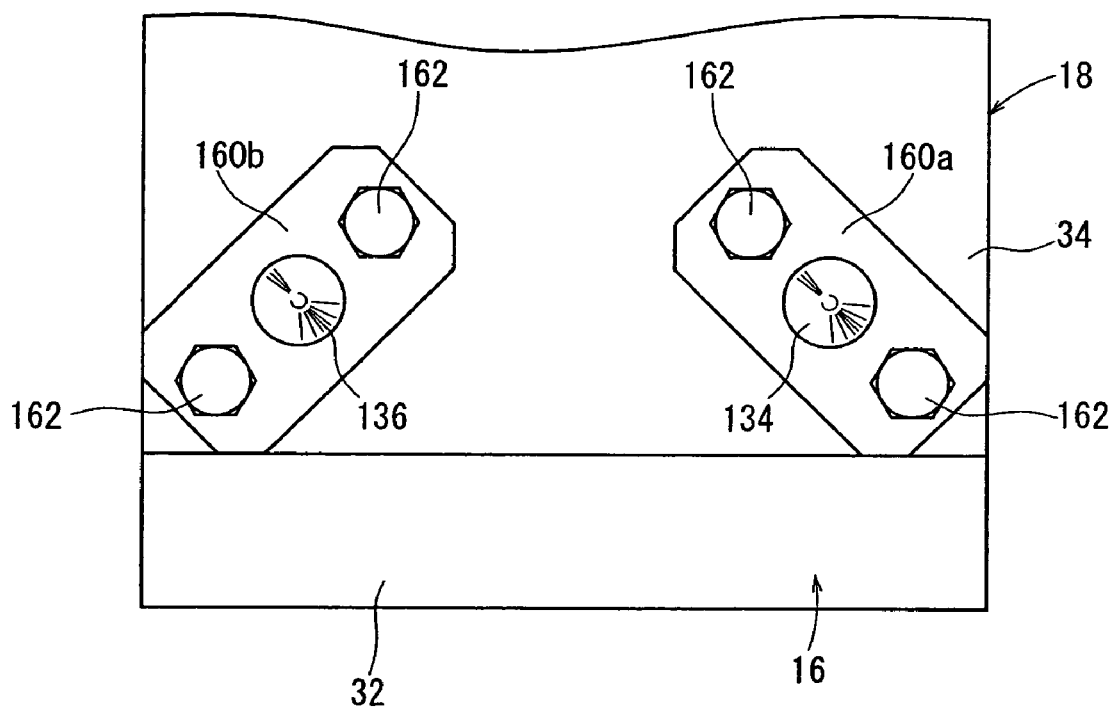
FIG. 9 is an enlarged left side elevational view of the storage casing of the second support post, as viewed from the left side of the image forming apparatus.

Guide plates 160a, 160b, 160c having respective guide holes 158a, 158b, 158c aligned with the second holes 156a, 156b, 156c, respectively, are mounted by bolts 162 on the opposite side walls of the storage casing 34 (see also FIGS. 8 and 9). The guide holes 158a, 158b, 158c have diameters substantially equal to those of the first, second, and third lock pins 134, 136, 150. When the first, second, and third lock pins 134, 136, 150 are inserted respectively into the guide holes 158a, 158b, 158c, the first, second, and third lock pins 134, 136, 150 are guided thereby for axial movement. The first, second, and third lock pins 134, 136, 150 that are inserted respectively into the guide holes 158a, 158b, 158c have tapered distal ends, respectively.

In the present embodiment, the second lock 102 selectively locks the second support post 18 and the main unit 20 to the vehicle 12 and unlocks the second support post 18 and the main unit 20 from the vehicle 12 when the grip lever 126 is manually turned. However, the first, second, and third holder blocks 138, 142, 152 may be replaced with solenoid-operated valves, and the solenoid-operated valves may be energized and de-energized for electrically locking the second support post 18 and the main unit 20 to the vehicle 12 and unlocking the second support post 18 and the main unit 20 from the vehicle 12.

Figure 12:
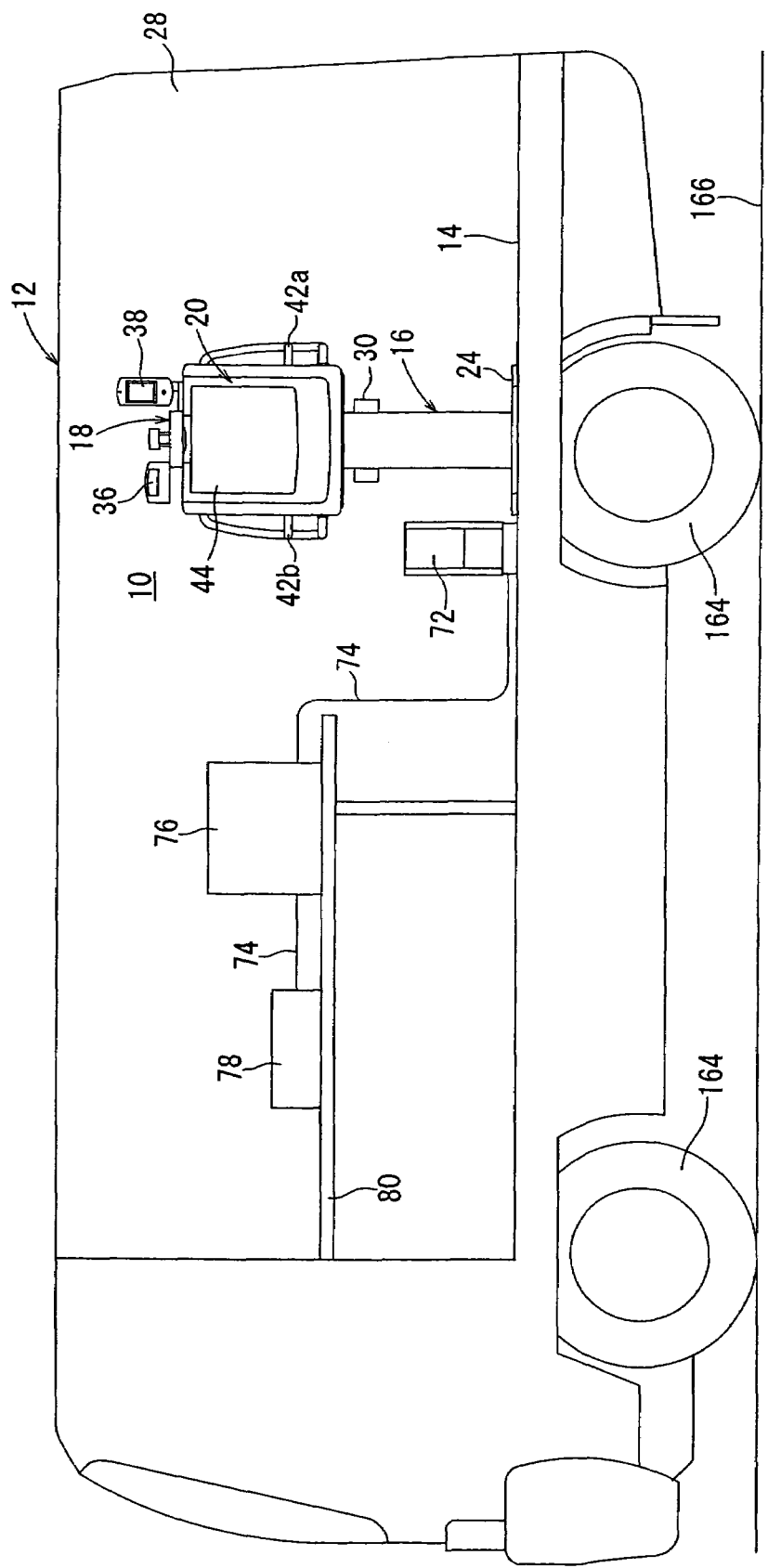
FIG. 12 is a schematic side elevational view showing a vehicle-mounted system including the image forming apparatus installed on the vehicle.

As shown in FIG. 12, a vehicle-mounted system which is installed in the compartment of the vehicle 12 includes an image processor 76 for confirming and processing image data and image information generated by the image forming apparatus 10, and a recorder 78 for saving image data and image information confirmed and processed by the image processor 76.

The image processor 76 is placed on the upper surface of a table 80 or the like and is connected to the controller 72 by a cable 74. The image processor 76 is also connected to the recorder 78 (e.g., a CD drive or a DVD drive) by a cable 74. If a printer (not shown) is connected to the image processor 76, then the printer can print image data and image information confirmed and processed by the image processor 76.

After image data and image information have been confirmed and processed by the image processor 76, these image data and image information may be saved to a recording medium (not shown) such as a CD or a DVD by the recorder 78. Then, the recording medium with the stored image data and image information may be carried out of the vehicle 12.

The image forming apparatus 10 according to the present embodiment is basically constructed as described above. Operation and advantages of the image forming apparatus 10 will be described below.

First, operation of the vibration isolation mechanism 22 to suppress vibrations transmitted from the vehicle 12 to the main unit 20 of the image forming apparatus 10 will be described below. In this case, the first and second locks 100, 102 of the fixing mechanism 23 release the main unit 20 and the second support post 18 from the vehicle 12 and the first support post 16 (see FIGS. 1 and 2).

As shown in FIG. 12, while the vehicle 12 is being driven along a road or other surface 166, vibrations from wheels 164 of the vehicle 12 are transmitted to the floor 14 and the wall 28 of the vehicle 12 and then to the first support post 16 that is fixed to the floor 14 and the wall 28.

The vibrations transmitted to the first support post 16 are applied to the vibration isolation mechanism 22, and dampened to a predetermined level by the springs of the spring 84 of the vibration isolation mechanism 22. The characteristics and the number of the springs of the spring 84 are established depending on the weights and the positions of the center of gravity of the second support post 18 and the main unit 20 which are swingably supported on the vibration isolation mechanism 22, or various conditions such as vibrating conditions of the vehicle 12 while the vehicle 12 is being driven. Consequently, the vibrations transmitted through the spring 84 are appropriately suppressed to a level small enough not to adversely affect the optical system in the main unit 20 that is supported on the second support post 18.

As a result, the vibrations from the vehicle 12 are essentially prevented from being transmitted to the second support post 18 that is joined to the first support post 16 by the vibration isolation mechanism 22, and hence to the main unit 20 supported on the second support post 18. Stated otherwise, when the vibrations from the vehicle 12 are transmitted through the first support post 16 to the vibration isolation mechanism 22, the vibrations are absorbed by the vibration isolation mechanism 22 and will not be applied directly to the second support post 18 and the main unit 20.

When the vehicle 12 is brought to a stop for capturing a radiation image of the subject 40 with the main unit 20 of the image forming apparatus 10, the main unit 20 which is swingably supported on the second support post 18 by the vibration isolation mechanism 22 needs to be securely joined to the vehicle 12 and the first support post 16 for protection against undesirable swinging displacement.

Operation of the fixing mechanism 23 to fix the second support post 18 which supports the main unit 20 thereon to the vehicle 12 and the first support post 16 will be described below.

As shown in FIG. 5, the grip lever 112 of the lock arm 106 is gripped and turned toward the wall 28 of the vehicle 12 in the direction indicated by the arrow A. The clamp 116 is turned toward the bracket 110 on the wall 28, and causes the engaging slot 114 to fit over the pin 108 of the bracket 110. The second support post 18 and the main unit 20 are now prevented from being displaced toward and away from the wall 28 in the directions of the X-axis by the lock arm 106 of the first lock 100 (see FIG. 6).

At the same time, since the clamp 116 is engaged by the opposite ends of the recess 118 defined substantially centrally in the pin 108, the second support post 18 and the main unit 20 are also prevented from being displaced substantially parallel to the wall 28 in the directions of the Y-axis. Thus, the second support post 18 on which the main unit 20 is supported is secured to the wall 28 by the first lock 100 against substantially horizontal displacement in the directions along the X- and Y-axes.

For securing the second support post 18 to the first support post 16 with the second lock 102 in the joint casing 32, as shown in FIG. 7, the grip lever 126 projecting from the joint casing 32 is gripped and turned upwardly from a substantially horizontal position toward the joint casing 32 in the direction indicated by the arrow C until the grip lever 126 lies substantially parallel to the confronting side wall of the joint casing 32 as indicated by the two-dot-and-dash lines in FIG. 7 (see FIG. 8).

As shown in FIG. 10, the shaft 122 pivotally coupled to the grip lever 126 is axially pushed into the joint casing 32 and displaced a predetermined distance along the direction indicated by the arrow Y1. The connector 130 coupled to the shaft 122 is displaced in the direction indicated by the arrow Y1, displacing the first and second lock pins 134, 136 axially in and along the through holes 140 in the first and second holder blocks 138, 142. As a result, the first and second lock pins 134, 136 are inserted through the first holes 154a, 154b of the joint casing 32 and the second holes 156a, 156b of the storage casing 34 into the respective guide holes 158a, 158b of the guide plates 160a, 160b. Since the first and second lock pins 134, 136 have the tapered distal ends, respectively, they can smoothly be inserted into the guide holes 158a, 158b.

At the same time, the displacement of the first lock pin 134 in the direction indicated by the arrow Y1 causes the end of the link arm 146 which is engaged by the first lock pin 134 to turn about the support pin 144 clockwise in the direction indicated by the arrow E (FIG. 10) away from the grip lever 126, and also causes the other end of the link arm 146 to turn about the support pin 144 clockwise in the direction indicated by the arrow E toward the third holder block 152.

The third lock pin 150 which engages the other end of the link arm 146 through the link pin 148b is pushed in the direction indicated by the arrow Y2 while being held by the third holder block 152. Therefore, the third lock pin 150 is axially displaced in and along the through hole 140 in the third holder block 152, and is inserted through the first hole 154c of the joint casing 32 and the second hole 156c of the storage casing 34 into the guide hole 158c of the guide plate 160c. Since the third lock pin 150 has the tapered distal end, it can smoothly be inserted into the guide hole 158c.

Inasmuch the first, second, and third lock pins 134, 136, 150 are inserted respectively into the guide holes 158a, 158b, 158c of the guide plates 160a, 160b, 160c through the first holes 154a, 154b, 154c and the second holes 156a, 156b, 156c, the joint casing 32 coupled to the first support post 16 and the storage casing 34 on the lower end of the second support post 18 are prevented from being displaced relatively to each other by the first, second, and third lock pins 134, 136, 150.

Specifically, since the first, second, and third lock pins 134, 136, 150 are inserted in the guide holes 158a, 158b, 158c which have respective diameters substantially equal to the outside diameters of the first, second, and third lock pins 134, 136, 150, the second support post 18 on which the guide plates 160a, 160b, 160c are mounted is prevented from being displaced in its axial directions along the Z-axis, and also from being displaced toward and away from the wall 28 in the directions along the X-axis.

That is, because the first support post 16 is fixed to the floor 14 of the vehicle 12 by the support base 24 and also to the wall 28 by the bracket 110, the second support post 18 fixed to the first support post 16 by the joint casing 32 is fixed to the vehicle 12.

Consequently, the main unit 20 that is supported on the second support post 18 is prevented by the first lock 100 from being displaced toward and away from the wall 28 in the directions along the X-axis and also from being displaced substantially parallel to the wall 28 in the directions along the Y-axis, and is prevented by the second lock 102 from being displaced in the axial directions of the second support post 18 along the Z-axis and also from being displaced toward and away from the wall 28 in the directions along the X-axis. Therefore, the main unit 20 is firmly fixed reliably to the vehicle 12 in the three-dimensional directions along the X-axis, the Y-axis, and the Z-axis by the fixing mechanism 23 having the first and second locks 100, 102.

Stated otherwise, while the vehicle 12 is being driven, the main unit 20 that is swingably supported on the first support post 16 by the vibration isolation mechanism 22 is not swingably displaced as it is reliably secured to the vehicle 12 by the fixing mechanism 23.

In the illustrated embodiment, it has been described that the main unit 20 and the second support post 18 are fixed to the vehicle 12 and the first support post 16 successively by the first lock 100 and the second lock 102 in the order named. However, the main unit 20 and the second support post 18 may be fixed to the vehicle 12 and the first support post 16 successively by the second lock 102 and the first lock 100 in the order named.

Operation of the image forming apparatus 10 fixed to the vehicle 12 with the second support post 18 and the main unit 20 locked by the fixing mechanism 23 against swinging displacement will be described below.

First, a process of recording radiation image information on a stimulable phosphor sheet IP will be described below. The reading/erasing unit 54 is held in a standby position at the lower end of its vertical moving stroke shown in FIG. 3. The stimulable phosphor sheet IP is positioned in the solid-line position close to the exposure base 46.

The operator operates the console panel 38 (see FIG. 1) on the second support post 18 and a control means (not shown) to move the main unit 20 vertically along the second post 18 to a position depending on the region of the subject 40 which is to be exposed. Then, the operator energizes the radiation source 48 to apply X-rays to the subject 40. The X-rays pass through the subject 40 and are applied through the phototimer 50 and the grid 52 to the stimulable phosphor sheet IP, recording radiation image information of the subject 40 on the stimulable phosphor sheet IP.

After the radiation image information is recorded on the stimulable phosphor sheet IP, the stimulable phosphor sheet IP is displaced from the solid-line position to the two-dot-and-dash-line position by a stimulable phosphor sheet moving motor (not shown). Then, the reading/erasing unit moving motor 68 is energized to cause the feed belts 66a, 66b to lift the reading/erasing unit 54, whereupon the reader 56 starts reading the radiation image information recorded on the stimulable phosphor sheet IP.

Specifically, the light sources 60 of the reader 56 emit stimulating light that is applied as a line of light to the stimulable phosphor sheet IP, as shown in FIG. 3. Upon exposure to the stimulating light, the stimulable phosphor sheet IP emits photostimulated luminescence commensurate with the radiation energy stored in the stimulable phosphor sheet IP. The emitted photostimulated luminescence is then converted by the CCD line sensors 62 that are positioned in a staggered array into an electric signal, which is processed and transmitted to the image processor 76. At this time, the reader 56 moves upwardly along the guide rails 70 to scan the stimulable phosphor sheet IP for thereby two-dimensionally reading the radiation image information that is recorded on the stimulable phosphor sheet IP over its entire area.

The reading/erasing unit 54 moves up to the upper end of its stroke, whereupon the reader 56 completes the reading of the radiation image information from the stimulable phosphor sheet IP. Thereafter, the reading/erasing unit 54 starts move downwardly, and the eraser 58 performs an erasing process. Specifically, the eraser 58 applies erasing light emitted from the light sources 64 to the stimulable phosphor sheet IP while the reading/erasing unit 54 is descending. In response to the erasing light applied to the stimulable phosphor sheet IP, the stimulable phosphor sheet IP discharges remaining radiation energy. This process continues until the reading/erasing unit 54 reaches the lower end of its stroke, whereupon the erasing of remaining radiation energy from the entire area of the stimulable phosphor sheet IP is completed.

As shown in FIG. 12, the image processor 76 confirms and processes image data and image information acquired from the stimulable phosphor sheet IP through the controller 72 connected to the image forming apparatus 10. The image data and image information may be saved to a CD or a DVD by the recorder 78, or may be printed by a printer (not shown).

After the above image forming process performed by the image forming apparatus 10 is finished, if the vehicle 12 is to be driven again, then it is necessary to release the second support post 18 and the main unit 20 from the vehicle 12 through the fixing mechanism 23, and to make the main unit 20 supported on the second support post 18 swingable on the first support post 16 through the vibration isolation mechanism 22 to prevent undue vibrations from being transmitted from the vehicle 12 to the second support post 18 and the main unit 20.

First, the grip lever 112 of the lock arm 106 of the first lock 100 shown in FIG. 6 is gripped and turned away from the wall 28 of the vehicle 12 in the direction indicated by the arrow B. The lock arm 106 is disengaged from the pin 108 of the bracket 110, whereupon the first lock 100 is released from the wall 28.

Stated otherwise, the second support post 18 and the main unit 20 which have been prevented from being displaced by the first lock 100 is rendered displaceable in the substantially horizontal directions along the X- and Y-axes.

For releasing the second support post 18 from the first support post 16 with the second lock 102, as shown in FIG. 7, the grip lever 126 tilted upwardly of the end of the shaft 122 is turned away from the joint casing 32 in the direction indicated by the arrow D in FIG. 7 to a substantially horizontal position.

The shaft 122 pivotally coupled to the grip lever 126 is axially pulled out of the joint casing 32 and displaced a predetermined distance along the direction indicated by the arrow Y2.

At the same time, the displacement of the first lock pin 134 in the direction indicated by the arrow Y2 causes the end of the link arm 146 which is engaged by the first lock pin 134 to turn about the support pin 144 counterclockwise in the direction indicated by the arrow F (FIG. 10) toward the grip lever 126, and also causes the other end of the link arm 146 to turn about the support pin 144 counterclockwise in the direction indicated by the arrow F away from the third holder block 152. The link arm 146 is thus turned, the third lock pin 150 that is coupled thereto by the link pin 148b is pulled in the direction indicated by the arrow Y1.

When the connector 130 coupled to the shaft 122 is displaced from the position shown in FIG. 11 in the direction indicated by the arrow Y2, the first and second lock pins 134, 136 are displaced axially in and along the through holes 140 in the first and second holder blocks 138, 142. As a result, the distal ends of the first and second lock pins 134, 136 which have been inserted in the respective guide holes 158a, 158b of the guide plates 160a, 160b are displaced into the first holes 154a, 154b.

At the same time, the third lock pin 150 is axially displaced in and along the through hole 140 in the third holder block 152, and the distal end of the third lock pin 150 which has been inserted in the guide hole 158c of the guide plate 160c is displaced into the first hole 154c.

That is, the distal ends of the first, second, and third lock pins 134, 136, 150 which have been inserted in the guide holes 158a, 158b, 158c and the second holes 156a, 156b, 156c are inserted only in the respective first holes 154a, 154b, 154c upon displacement of the first, second, and third lock pins 134, 136, 150 into the joint casing 32. Therefore, the second support post 18 which has been prevented from being displaced with respect to the joint casing 32 by the first, second, and third lock pins 134, 136, 150 is now released from the joint casing 32.

Therefore, the main unit 20 that is supported on the second support post 18 is released from the locked state in which it has been prevented by the first lock 100 from being displaced toward and away from the wall 28 in the directions along the X-axis and also from being displaced substantially parallel to the wall 28 in the directions along the Y-axis, and is prevented from the locked state in which it has been prevented by the second lock 102 from being displaced in the axial directions of the second support post 18 along the Z-axis and also from being displaced toward and away from the wall 28 in the directions along the X-axis.

Consequently, the main unit 20 is rendered swingable in the three-dimensional directions along the X-axis, the Y-axis, and the Z-axis by the vibration isolation mechanism 22 which is disposed between the second support post 18 and the first support post 16.

In the illustrated embodiment, it has been described that the main unit 20 and the second support post 18 are released from the locked state successively by the first lock 100 and the second lock 102 in the order named. However, the main unit 20 and the second support post 18 may be released from the locked state successively by the second lock 102 and the first lock 100 in the order named.

For capturing an image of the subject 40 with the image forming apparatus 10, as described above, the second support post 18 and the main unit 20 are released from the vehicle 12. When the vehicle 12 with the image forming apparatus 10 installed thereon is driven, even if vibrations from the vehicle 12 are transmitted to the first support post 16, the vibrations are dampened by the springs of the spring 84 of the vibration isolation mechanism 22, and hence any vibrations transmitted from the first support post 16 to the second support post 18 are suppressed.

At this time, the level of vibrations dampened by the vibration isolation mechanism 22 and transmitted from the first support post 16 to the second support post 18 is reduced to a numerical value small enough not to adversely affect the optical system in the main unit 20. Therefore, undue vibrations generated when the vehicle 12 with the high resolution image forming apparatus 10 installed thereon is driven are prevented from being transmitted to the main unit 20. After the vehicle 12 with the image forming apparatus 10 installed thereon has traveled a certain distance, the image forming apparatus 10 is capable of taking pictures of the subject 40.

Specifically, while the vehicle 12 with the image forming apparatus 10 is being driven, the second support post 18 and the main unit 20 are released from the vehicle 12 and the first support post 16, so that the second support post 18 supporting the main unit 20 is allowed to be swingably displaced with respect to the first support post 16 and the vehicle 12. When the vehicle 12 is stopped to form an image with the image forming apparatus 10, the second support post 18 and the main unit 20 are fixed to the vehicle 12 and the first support post 16 by the fixing mechanism 23, so that the main unit 20 is prevented from being swingably displaced.

The image forming apparatus 10 according to the present embodiment employs a CR system which uses the stimulable phosphor sheet IP in the main unit 20 for storing part of radiation energy and emitting photostimulated luminescence commensurate with the stored energy in response to stimulating light such as a laser beam, visible light, or the like. However, the present invention is not limited to the CR system, but may be applicable to a solid-state sensor system such as a FPD (Flat Panel Detector) or the like capable of converting detected X-ray energy into an electric signal for producing an image.

When the vehicle 12 is stopped to capture an image of the subject 40, if the second support post 18 is not fixed to the vehicle 12 by the first and second locks 100, 102 of the fixing mechanism 23, then an activation lock mechanism may be operated to determine, with the controller 72 or a software program, how the lock arm 106 of the first lock 100 and the grip lever 126 of the second lock 102 are operated, and prevent the image forming apparatus 10 from being activated.

The activation lock mechanism prevents the image forming apparatus 10 from being activated if the operator forgets to fix the main unit 20 to the vehicle 12 with the fixing mechanism 23. Therefore, the main unit 20 that is not locked against swinging movement is prevented from capturing an image of the subject 40.

Another way of preventing the operator from forgetting to lock the main unit 20 to the vehicle 12 or unlock the main unit 20 from the vehicle 12 is to display error information indicating that the second support post 18 is not fixed to the first support post 16, on the display unit 36 under the control of the controller 72, or to produce an alarm sound from a speaker (not shown) or the like under the control of the controller 72, thereby warning the operator that the main unit 20 is not locked or unlocked by the fixing mechanism 23.

As a consequence, the operator is prevented from forgetting to lock the main unit 20 to the vehicle 12 with the fixing mechanism 23, thereby preventing the main unit 20 and the second support post 18 from being swingably displaced when a picture of the subject 40 is captured. The operator is also prevented from forgetting to unlock the main unit 20 from the vehicle 12 with the fixing mechanism 23, thereby preventing undue vibrations from being transmitted from the vehicle 12 directly to the image forming apparatus 10.

Furthermore, when the image forming apparatus 10 is activated, the main unit 20 may automatically be locked to the vehicle 12 by the fixing mechanism 23, and when the image forming apparatus 10 is inactivated, the main unit 20 may automatically be unlocked from the vehicle 12 by the fixing mechanism 23. With this arrangement, even if the operator forgets to lock the main unit 20 to the vehicle 12 or unlock the main unit 20 from the vehicle 12 with the fixing mechanism 23, undue vibrations are prevented from being transmitted from the vehicle 12 directly to the image forming apparatus 10, and the main unit 20 is prevented from being swingably displaced when an image of the subject 40 is captured.

According to the present embodiment, as described above, the image forming apparatus 10 has the vibration isolation mechanism 22 for preventing vibrations produced when the vehicle 12 is driven from being transmitted to the main unit 20, disposed between the first support post 16 fixed to the floor 14 in the compartment of the vehicle 12 and the second support post 18 which supports the main unit 20 for capturing an image of the subject 40.

The second support post 18 which is swingably supported by the vibration isolation mechanism 22 has the first lock 100 for fixing the second support post 18 to the wall 28 of the vehicle 12, and the joint casing 32 of the first support post 16 has the second lock 102 disposed therein for fixing the second support post 18 to the first support post 16.

When the vehicle 12 is stopped to capture an image of the subject 40, the main unit 20 held by the vibration isolation mechanism 22 needs to be prevented from being swingably displaced with respect to the vehicle 12 and the first support post 16. Therefore, the lock arm 106 of the first lock 100 is turned into engagement with the bracket 110 mounted on the wall 28 of the vehicle 12, thus securing the second support post 18 and the main unit 20 integrally to the vehicle 12.

In addition, the grip lever 126 of the second lock 102 is turned to displace the first, second, and third lock pins 134, 136, 150 axially in the directions indicated by the arrows Y1, Y2 through the first holes 154a, 154b, 154c of the joint casing 32 and the second holes 156a, 156b, 156c of the storage casing 34 into the guide holes 158a, 158b, 158c of the guide plates 160a, 160b, 160c.

Since the joint casing 32 of the first support post 16 that is fixed to the vehicle 12 and the storage casing 34 of the second support post 18 are firmly joined to each other, the main unit 20 supported on the second support post 18 is locked against swinging displacement.

When an image of the subject 40 is captured and the vehicle 12 is to be driven again, the lock arm 106 of the first lock 100 and the grip lever 126 of the second lock 102 are turned in the directions opposite to the directions described above, thereby locking the second support post 18 again to the vehicle 12.

Therefore, the second support post 18 which is swingably be supported by the vibration isolation mechanism 22 can be fixed to the vehicle 12 and the first support post 16 and released from the vehicle 12 simply by turning the lock arm 106 of the first lock 100 and the grip lever 126 of the second lock 102.

While the vehicle 12 is being driven, the main unit 20 is released from the vehicle 12 by the fixing mechanism 23, thereby preventing vibrations from being transmitted from the vehicle 12 to the second support post 18 which supports the main unit 20 with the vibration isolation mechanism 22. For capturing an image of the subject 40 on the vehicle 12 which is held at rest, the main unit 20 is fixed to the vehicle 12 by the fixing mechanism 23, and can capture an image of the subject 40 in an ordinary fashion. The fixing mechanism 23 is thus easily capable of selectively fixing the second support post 18 and the main unit 20 to the vehicle 12 and releasing the second support post 18 and the main unit 20 from the vehicle 12.

Although a certain preferred embodiment of the present invention has been shown and described in detail, it should be understood that various changes and modifications may be made therein without departing from the scope of the appended claims.

What is claimed is:

1. A fixing structure for an image forming apparatus, comprising:
    a vehicle including a means for movably supporting the vehicle on a surface;
    an exposure unit permanently disposed in a compartment of the vehicle, for applying a radiation to a subject and capturing a radiation image of the subject;
    a support post fixedly mounted in the compartment of the vehicle;
    a holder for holding said exposure unit;
    a vibration isolation mechanism for connecting said support post and said holder to each other to dampen vibrations transmitted from said vehicle to said support post for thereby preventing vibrations from being transmitted to said holder; and
    a fixing mechanism for fixing said holder to said vehicle or said support post and releasing said holder from said vehicle or said support post;
    wherein when said vehicle is stopped for said exposure unit to capture a radiation image of the subject, said fixing mechanism fixes said holder to said vehicle or said support post, and when said vehicle is to be driven, said fixing mechanism releases said holder from said vehicle or said support post,
    wherein said fixing mechanism comprises a first fixture mounted on said holder for fixing said holder to a wall in the compartment of said vehicle; and a second fixture disposed between said support post and said holder for fixing said holder to said support post,
    wherein said second fixture comprises an operating lever angularly movably mounted on said support post; and lock pins responsive to angular movement of said operating lever for axial displacement through first holes defined in said support post and second holes defined in said holder,
    wherein said lock pins extend substantially parallel to each other, and one of said lock pins and another thereof are displaceable in opposite axial directions in response to the angular movement of said operating lever.

2. A fixing structure according to claim 1, wherein the means for moveably supporting the vehicle includes at least one wheel.

3. A fixing structure for an image forming apparatus, comprising:
    a vehicle including a means for movably supporting the vehicle on a surface;
    an exposure unit permanently disposed in a compartment of the vehicle, for applying a radiation to a subject and capturing a radiation image of the subject;
    a support post fixedly mounted in the compartment of the vehicle;
    a holder for holding said exposure unit;
    a vibration isolation mechanism for connecting said support post and said holder to each other to dampen vibrations transmitted from said vehicle to said support post for thereby preventing vibrations from being transmitted to said holder; and
    a fixing mechanism for fixing said holder to said vehicle or said support post and releasing said holder from said vehicle or said support post;
    wherein when said vehicle is stopped for said exposure unit to capture a radiation image of the subject, said fixing mechanism fixes said holder to said vehicle or said support post, and when said vehicle is to be driven, said fixing mechanism releases said holder from said vehicle or said support post,
    wherein said fixing mechanism comprises a first fixture mounted on said holder for fixing said holder to a wall in the compartment of said vehicle; and a second fixture disposed between said support post and said holder for fixing said holder to said support post,
    wherein said second fixture comprises an operating lever angularly movably mounted on said support post; and lock pins responsive to angular movement of said operating lever for axial displacement through first holes defined in said support post and second holes defined in said holder,
    wherein said lock pins are connected to each other by a link arm that is angularly movable with respect to said support post and that is operatively coupled to said operating lever.

4. A fixing structure according to claim 3, wherein the means for moveably supporting the vehicle includes at least one wheel.

5. A fixing structure for an image forming apparatus, comprising:
    an exposure unit disposed in a compartment of a vehicle, for applying a radiation to a subject and capturing a radiation image of the subject;
    a support post fixedly mounted in the compartment of the vehicle;
    a holder for holding said exposure unit;
    a vibration isolation mechanism for connecting said support post and said holder to each other to dampen vibrations transmitted from said vehicle to said support post for thereby preventing vibrations from being transmitted to said holder; and a fixing mechanism for fixing said holder to said vehicle or said support post and releasing said holder from said vehicle or said support post;

wherein when said vehicle is stopped for said exposure unit to capture a radiation image of the subject, said fixing mechanism fixes said holder to said vehicle or said support post, and when said vehicle is to be driven, said fixing mechanism releases said holder from said vehicle or said support post, wherein said fixing mechanism comprises a first fixture mounted on said holder for fixing said holder to a wall in the compartment of said vehicle; and a second fixture disposed between said support post and said holder for fixing said holder to said support post, wherein said second fixture comprises an operating lever angularly movably mounted on said support post; and lock pins responsive to angular movement of said operating lever for axial displacement through first holes defined in said support post and second holes defined in said holder, wherein said lock pins extend substantially parallel to each other, and one of said lock pins and another thereof are displaceable in opposite axial directions in response to the angular movement of said operating lever.

6. A fixing structure according to claim 5, wherein said first fixture comprises:

a clamp arm angularly movably mounted on said holder and including a slot for engaging an engaging member mounted on said wall in the compartment of said vehicle.

7. A fixing structure according to claim 6, wherein said engaging member includes an engaging pin for being engaged by said clamp arm through said slot, said engaging pin having a recess defined therein and extending axially over a predetermined distance for engagement with said clamp arm through said slot.

8. A fixing structure according to claim 5, wherein when said holder is to be fixed to said support post, said lock pins are inserted into said first holes and said second holes in response to the angular movement of said operating lever, and when said holder is to be released from said support post, said lock pins are removed from at least either said first holes or said second holes.

9. A fixing structure according to claim 5, wherein the number of said first holes is equal to the number of said second holes.

10. A fixing structure for an image forming apparatus, comprising:

an exposure unit disposed in a compartment of a vehicle, for applying a radiation to a subject and capturing a radiation image of the subject;

a support post fixedly mounted in the compartment of the vehicle;

a holder for holding said exposure unit;

a vibration isolation mechanism for connecting said support post and said holder to each other to dampen vibrations transmitted from said vehicle to said support post for thereby preventing vibrations from being transmitted to said holder; and a fixing mechanism for fixing said holder to said vehicle or said support post and releasing said holder from said vehicle or said support post;

wherein when said vehicle is stopped for said exposure unit to capture a radiation image of the subject, said fixing mechanism fixes said holder to said vehicle or said support post, and when said vehicle is to be driven, said fixing mechanism releases said holder from said vehicle or said support post, wherein said fixing mechanism comprises a first fixture mounted on said holder for fixing said holder to a wall in the compartment of said vehicle; and a second fixture disposed between said support post and said holder for fixing said holder to said support post, wherein said second fixture comprises an operating lever angularly movably mounted on said support post; and lock pins responsive to angular movement of said operating lever for axial displacement through first holes defined in said support post and second holes defined in said holder, wherein said lock pins are connected to each other by a link arm that is angularly movable with respect to said support post and that is operatively coupled to said operating lever.

11. A fixing structure according to claim 10, wherein said first fixture comprises:

a clamp arm angularly movably mounted on said holder and including a slot for engaging an engaging member mounted on said wall in the compartment of said vehicle.

12. A fixing structure according to claim 11, wherein said engaging member includes an engaging pin for being engaged by said clamp arm through said slot, said engaging pin having a recess defined therein and extending axially over a predetermined distance for engagement with said clamp arm through said slot.

13. A fixing structure according to claim 10, wherein when said holder is to be fixed to said support post, said lock pins are inserted into said first holes and said second holes in response to the angular movement of said operating lever, and when said holder is to be released from said support post, said lock pins are removed from at least either said first holes or said second holes.

14. A fixing structure according to claim 10, wherein the number of said first holes is equal to the number of said second holes.

* * * * *